US012478449B1

(12) United States Patent
Vitello et al.

(10) Patent No.: US 12,478,449 B1
(45) **Date of Patent: *Nov. 25, 2025**

(54) NEEDLE PACKAGING AND DISPOSAL ASSEMBLY

(71) Applicant: International Medical Industries Inc., Pompano Beach, FL (US)

(72) Inventors: Patrick Vitello, Pompano Beach, FL (US); Jonathan Vitello, Fort Lauderdale, FL (US); Peter Lehel, Boca Raton, FL (US)

(73) Assignee: INTERNATIONAL MEDICAL INDUSTRIES INC, Pompano Beach, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/234,810

(22) Filed: Aug. 16, 2023

Related U.S. Application Data

(63) Continuation of application No. 17/840,442, filed on Jun. 14, 2022, now abandoned, which is a (Continued)

(51) Int. Cl.
*A61B 50/36* (2016.01)
*B65D 75/36* (2006.01)

(52) U.S. Cl.
CPC .......... *A61B 50/362* (2016.02); *B65D 75/366* (2013.01)

(58) Field of Classification Search
CPC .. A61B 50/362; A61B 50/3001; B65D 75/366
(Continued)

(56) References Cited

U.S. PATENT DOCUMENTS 722,943 A 3/1903 Chappell
732,662 A 6/1903 Smith
(Continued)

FOREIGN PATENT DOCUMENTS

DE 202008018507 2/2015
EP 0148116 7/1985
(Continued)

OTHER PUBLICATIONS

Arai Tsugio, Pilfering Proof Cap, Jan. 9, 1996.

*Primary Examiner* — Jacob K Ackun
(74) *Attorney, Agent, or Firm* — Malloy & Malloy, PL; Jennie S. Malloy

(57) ABSTRACT

An assembly, for packaging and safely disposing of a needle structure, including a housing having at least one containment structure. The containment structure includes a hinge movably interconnecting a base and a needle retaining segment, between open and closed orientations. The retaining segment includes a compartment removably containing the needle structure therein and the base includes a chamber for reception of the compartment and medical needle therein, when in the closed orientation. The hinge normally biases the retaining segment and compartment outwardly at substantially a predetermined angular orientation relative to the base, in the open orientation, to facilitate access to the medical needle through an access opening in the compartment. A closure is fixedly connected to and movable with both the base and the retaining segment and is structured to removably secure the housing in the closed orientation.

19 Claims, 4 Drawing Sheets

Related U.S. Application Data continuation of application No. 17/104,807, filed on Nov. 25, 2020, now Pat. No. 11,357,588.

(60) Provisional application No. 62/939,958, filed on Nov. 25, 2019.

(58) Field of Classification Search
USPC .......................................... 206/364, 365, 366
See application file for complete search history.

(56) References Cited

U.S. PATENT DOCUMENTS 1,678,991 A 7/1928 Marschalek
1,970,631 A 8/1934 Sherman
2,186,888 A 1/1940 Tullar et al.
2,277,936 A 3/1942 Rosenblatt
2,459,304 A 1/1949 Blank
2,477,598 A 8/1949 Hain
2,734,665 A 2/1956 Flamm
2,739,590 A 3/1956 Yochem
2,811,283 A 10/1957 Bowen
2,823,674 A 2/1958 Yochem
2,834,346 A 5/1958 Adams
2,875,761 A 3/1959 Helmer et al.
2,888,015 A 5/1959 Hunt
2,952,255 A 9/1960 Hein, Jr.
3,122,280 A 2/1964 Goda
3,180,532 A 4/1965 Michel
3,245,567 A 4/1966 Knight
3,301,256 A 1/1967 Cowley
3,323,798 A 6/1967 Miller
3,364,890 A 1/1968 Andersen
3,368,673 A 2/1968 Johnson
3,489,268 A 1/1970 Meierhoefer
3,568,673 A 3/1971 Cowley
3,574,306 A 4/1971 Alden
3,598,120 A 8/1971 Mass
3,610,241 A 10/1971 LeMarie
3,674,181 A 7/1972 Marks et al.
3,700,215 A 10/1972 Hardman et al.
3,706,307 A 12/1972 Hasson
3,712,749 A 1/1973 Roberts
3,726,445 A 4/1973 Ostrowsky et al.
3,747,751 A 7/1973 Miller et al.
3,850,329 A 11/1974 Robinson
3,872,867 A 3/1975 Killinger
3,904,033 A 9/1975 Haerr
3,905,375 A 9/1975 Toyama
3,937,211 A 2/1976 Merten
3,987,930 A 10/1976 Fuson
4,005,739 A 2/1977 Winchell
4,027,669 A 6/1977 Johnston et al.
4,043,334 A 8/1977 Brown et al.
4,046,145 A 9/1977 Choksi et al.
4,068,696 A 1/1978 Winchell
4,085,845 A 4/1978 Perfect
4,106,621 A * 8/1978 Sorenson ............. B65D 75/328 229/125.35
4,216,585 A 8/1980 Hatter
4,216,872 A 8/1980 Bean
4,220,151 A 9/1980 Whitney
4,244,366 A 1/1981 Raines
4,252,122 A 2/1981 Halvorsen
4,271,972 A 6/1981 Thor
4,286,591 A 9/1981 Raines
4,286,640 A 9/1981 Knox et al.
4,313,539 A 2/1982 Raines
4,369,781 A 1/1983 Gilson et al.
4,420,085 A 12/1983 Wilson et al.
4,430,077 A 2/1984 Mittleman et al.
4,433,790 A 2/1984 Gibson
4,457,445 A 7/1984 Hanks et al.
4,482,071 A 11/1984 Ishiwatari
D277,783 S 2/1985 Beck
4,520,942 A 6/1985 Dwinell
4,521,237 A 6/1985 Logothetis
4,530,437 A 7/1985 Gray et al.
4,530,697 A 7/1985 Kuhlemann et al.
4,558,554 A 12/1985 Herbert
4,571,242 A 2/1986 Klien et al.
4,589,171 A 5/1986 McGill
4,664,259 A 5/1987 Landis
4,667,837 A 5/1987 Vitello et al.
4,676,530 A 6/1987 Nordgren et al.
4,693,707 A 9/1987 Dye
4,726,483 A 2/1988 Drozd
4,735,617 A 4/1988 Nelson et al.
4,742,910 A 5/1988 Staebler
4,743,229 A 5/1988 Chu
4,743,231 A 5/1988 Kay et al.
4,753,345 A 6/1988 Goodsir et al.
4,760,847 A 8/1988 Vaillancourt
4,813,564 A 3/1989 Cooper et al.
4,832,695 A 5/1989 Rosenberg et al.
4,834,706 A 5/1989 Beck et al.
4,842,592 A 6/1989 Caggiani et al.
4,844,906 A 7/1989 Hermelin et al.
4,863,451 A 9/1989 Marder
4,906,231 A 3/1990 Young
4,919,285 A 4/1990 Roof et al.
4,936,445 A 6/1990 Grabenkort
5,007,535 A 4/1991 Meseke et al.
5,009,323 A 4/1991 Montgomery et al.
5,024,323 A 6/1991 Bolton
5,049,129 A 9/1991 Zdeb et al.
5,057,093 A 10/1991 Clegg et al.
D323,392 S 1/1992 Bryne
5,078,696 A 1/1992 Nedbaluk
5,085,332 A 2/1992 Gettig et al.
5,090,564 A 2/1992 Chimienti
5,119,975 A 6/1992 Jemielita
5,133,454 A * 7/1992 Hammer ............. A61M 5/3205 206/364
5,135,496 A 8/1992 Vetter et al.
5,148,652 A 9/1992 Herzog
5,163,922 A 11/1992 McElveen, Jr. et al.
5,165,560 A 11/1992 Ennis et al.
5,230,429 A 7/1993 Etheredge, III
5,267,983 A 12/1993 Oilschlager et al.
5,292,308 A 3/1994 Ryan
5,293,993 A * 3/1994 Yates, Jr. ............ A61M 5/3205 206/470
5,295,599 A 3/1994 Smith
5,312,367 A 5/1994 Nathan
5,312,368 A 5/1994 Haynes
5,316,163 A 5/1994 von Schuckmann
5,328,466 A 7/1994 Denmark
5,328,474 A 7/1994 Raines
5,332,113 A 7/1994 Kusler, III et al.
5,356,380 A 10/1994 Hoekwater et al.
5,370,226 A 12/1994 Gollobin et al.
5,380,295 A 1/1995 Vacca
5,402,887 A 4/1995 Shillington
5,405,339 A 4/1995 Kohnen et al.
5,456,668 A 10/1995 Ogle, II
5,458,580 A 10/1995 Hajishoreh
5,468,224 A 11/1995 Souryal
5,474,178 A 12/1995 DiViesti et al.
5,505,705 A 4/1996 Galpin et al.
5,531,695 A 7/1996 Swisher
5,540,324 A * 7/1996 Knapp ................... B65D 75/22 206/348
5,540,666 A 7/1996 Barta et al.
5,549,571 A 8/1996 Sak
5,558,648 A 9/1996 Shields
5,584,817 A 12/1996 van den Haak
5,588,239 A 12/1996 Anderson
5,611,445 A 3/1997 Kano et al.
5,617,954 A 4/1997 Kato et al.
5,624,402 A 4/1997 Imbert
5,662,233 A 9/1997 Reid
5,674,209 A 10/1997 Yarger
5,695,470 A 12/1997 Roussigne et al.

(56) References Cited

U.S. PATENT DOCUMENTS

| | | | | | |
|---|---|---|---|---|---|
| 5,699,913 | A | * | 12/1997 | Richardson | B65D 73/0071 40/658 |
| 5,700,247 | A | | 12/1997 | Grimard et al. | |
| 5,702,374 | A | | 12/1997 | Johnson | |
| 5,706,985 | A | | 1/1998 | Feer | |
| 5,711,443 | A | | 1/1998 | Bennett | |
| 5,713,485 | A | | 2/1998 | Liff et al. | |
| 5,776,124 | A | | 7/1998 | Wald | |
| 5,785,691 | A | | 7/1998 | Vetter et al. | |
| 5,797,885 | A | | 8/1998 | Rubin | |
| 5,807,343 | A | | 9/1998 | Tucker et al. | |
| 5,829,589 | A | | 11/1998 | Nguyen et al. | |
| D402,766 | S | | 12/1998 | Smith et al. | |
| 5,842,567 | A | * | 12/1998 | Rowe | A61B 50/3001 206/464 |
| 5,876,381 | A | * | 3/1999 | Pond | A61M 5/3216 128/919 |
| 5,883,806 | A | | 3/1999 | Meador et al. | |
| 5,884,457 | A | | 3/1999 | Ortiz et al. | |
| 5,901,866 | A | | 5/1999 | Storar | |
| 5,902,269 | A | | 5/1999 | Jentzen | |
| 5,926,922 | A | | 7/1999 | Stottle | |
| 5,951,522 | A | | 9/1999 | Rosato et al. | |
| 5,951,525 | A | | 9/1999 | Thorne et al. | |
| 5,954,203 | A | * | 9/1999 | Marconi | B65D 81/022 206/464 |
| 5,954,657 | A | | 9/1999 | Rados | |
| 5,957,166 | A | | 9/1999 | Safabash | |
| 5,957,314 | A | | 9/1999 | Nishida et al. | |
| 5,963,136 | A | | 10/1999 | O'Brien | |
| 5,983,596 | A | | 11/1999 | Corniani et al. | |
| 5,989,227 | A | | 11/1999 | Vetter et al. | |
| 5,993,437 | A | | 11/1999 | Raoz | |
| 6,000,548 | A | | 12/1999 | Tsals | |
| D419,671 | S | | 1/2000 | Jansen | |
| 6,021,824 | A | | 2/2000 | Larsen et al. | |
| 6,027,482 | A | | 2/2000 | Imbert | |
| 6,068,614 | A | | 5/2000 | Kimber et al. | |
| D430,293 | S | | 8/2000 | Jansen | |
| 6,112,951 | A | | 9/2000 | Mueller | |
| D431,864 | S | | 10/2000 | Jansen | |
| 6,126,640 | A | | 10/2000 | Tucker et al. | |
| 6,190,364 | B1 | | 2/2001 | Imbert | |
| 6,193,688 | B1 | | 2/2001 | Balestracci et al. | |
| 6,196,593 | B1 | | 3/2001 | Petrick et al. | |
| 6,196,998 | B1 | | 3/2001 | Jansen et al. | |
| 6,216,885 | B1 | | 4/2001 | Guillaume | |
| 6,235,376 | B1 | | 5/2001 | Miyazaki et al. | |
| 6,279,746 | B1 | | 8/2001 | Hussaini et al. | |
| 6,280,418 | B1 | | 8/2001 | Reinhard et al. | |
| 6,287,671 | B1 | | 9/2001 | Bright et al. | |
| 6,322,543 | B1 | | 11/2001 | Singh et al. | |
| 6,325,227 | B1 | | 12/2001 | Ekkert | |
| 6,338,200 | B1 | | 1/2002 | Baxa et al. | |
| 6,358,241 | B1 | * | 3/2002 | Shapeton | A61B 18/1402 606/1 |
| 6,375,640 | B1 | | 4/2002 | Teraoka | |
| 6,394,983 | B1 | | 5/2002 | Mayoral et al. | |
| 6,439,276 | B1 | | 8/2002 | Wood et al. | |
| 6,485,460 | B2 | | 11/2002 | Eakins et al. | |
| 6,488,666 | B1 | | 12/2002 | Geist | |
| 6,491,665 | B1 | | 12/2002 | Vetter et al. | |
| 6,500,155 | B2 | | 12/2002 | Sasso | |
| 6,520,935 | B1 | | 2/2003 | Jansen et al. | |
| 6,540,697 | B2 | | 4/2003 | Chen | |
| 6,565,529 | B1 | | 5/2003 | Kimber et al. | |
| 6,581,792 | B1 | | 6/2003 | Limanjaya | |
| 6,585,691 | B1 | | 7/2003 | Vitello | |
| 6,592,251 | B2 | | 7/2003 | Edwards et al. | |
| 6,666,852 | B2 | | 12/2003 | Niedospial, Jr. | |
| 6,682,798 | B1 | | 1/2004 | Kiraly | |
| 6,726,652 | B2 | | 4/2004 | Eakins et al. | |
| 6,726,672 | B1 | | 4/2004 | Hanly et al. | |
| 6,764,469 | B2 | | 7/2004 | Broselow | |
| 6,796,586 | B2 | | 9/2004 | Werth | |
| 6,821,268 | B2 | | 11/2004 | Balestracci | |
| D501,549 | S | | 2/2005 | McAllister et al. | |
| 6,921,383 | B2 | | 7/2005 | Vitello | |
| 6,935,560 | B2 | | 8/2005 | Andreasson et al. | |
| 6,942,643 | B2 | | 9/2005 | Eakins et al. | |
| 6,991,126 | B2 | | 1/2006 | Jackel | |
| 7,036,661 | B2 | | 5/2006 | Anthony et al. | |
| 7,055,273 | B2 | | 6/2006 | Roshkoff | |
| 7,100,771 | B2 | | 9/2006 | Massengale et al. | |
| 7,125,397 | B2 | | 10/2006 | Woehr et al. | |
| 7,141,286 | B1 | | 11/2006 | Kessler et al. | |
| 7,175,081 | B2 | | 2/2007 | Andreasson et al. | |
| 7,182,256 | B2 | | 2/2007 | Andreasson et al. | |
| 7,232,066 | B2 | | 6/2007 | Anderasson et al. | |
| 7,240,926 | B2 | | 7/2007 | Dalle et al. | |
| 7,299,981 | B2 | | 11/2007 | Hickle et al. | |
| 7,367,964 | B2 | | 5/2008 | Heinz et al. | |
| 7,374,555 | B2 | | 5/2008 | Heinz et al. | |
| 7,404,500 | B2 | | 7/2008 | Marteau et al. | |
| 7,410,803 | B2 | | 8/2008 | Nollert et al. | |
| 7,425,208 | B1 | | 9/2008 | Vitello | |
| 7,437,972 | B2 | | 10/2008 | Yeager | |
| 7,438,704 | B1 | | 10/2008 | Kawashima et al. | |
| D581,046 | S | | 11/2008 | Sudo | |
| D581,047 | S | | 11/2008 | Koshidaka | |
| D581,049 | S | | 11/2008 | Sudo | |
| 7,482,166 | B2 | | 1/2009 | Nollert et al. | |
| D589,612 | S | | 3/2009 | Sudo | |
| 7,497,330 | B2 | | 3/2009 | Anthony et al. | |
| 7,503,453 | B2 | | 3/2009 | Cronin et al. | |
| 7,588,563 | B2 | | 9/2009 | Guala | |
| 7,594,681 | B2 | | 9/2009 | DeCarlo | |
| 7,608,057 | B2 | | 10/2009 | Woehr et al. | |
| 7,611,487 | B2 | | 11/2009 | Woehr et al. | |
| 7,632,244 | B2 | | 12/2009 | Buehler et al. | |
| D608,900 | S | | 1/2010 | Giraud et al. | |
| 7,641,636 | B2 | | 1/2010 | Moesli et al. | |
| D612,939 | S | | 3/2010 | Boone, III et al. | |
| 7,681,606 | B2 | | 3/2010 | Khan et al. | |
| 7,698,180 | B2 | | 4/2010 | Fago et al. | |
| 7,708,035 | B2 | | 5/2010 | Windmiller | |
| 7,735,664 | B1 | | 6/2010 | Peters et al. | |
| 7,748,892 | B2 | | 7/2010 | McCoy | |
| 7,762,988 | B1 | | 7/2010 | Vitello | |
| 7,766,919 | B2 | | 8/2010 | Delmotte | |
| 7,802,313 | B2 | | 9/2010 | Czajka | |
| 7,886,908 | B2 | | 2/2011 | Farrar et al. | |
| 7,918,830 | B2 | | 4/2011 | Langan et al. | |
| 7,922,213 | B2 | | 4/2011 | Werth | |
| 7,988,004 | B1 | | 8/2011 | Marret et al. | |
| 8,034,041 | B2 | | 10/2011 | Domkowski et al. | |
| 8,079,518 | B2 | | 12/2011 | Turner et al. | |
| 8,091,727 | B2 | | 1/2012 | Domkowwski | |
| 8,118,788 | B2 | | 2/2012 | Frezza | |
| 8,120,484 | B2 | | 2/2012 | Chisholm | |
| 8,128,605 | B2 | | 3/2012 | Masi et al. | |
| 8,137,324 | B2 | | 3/2012 | Bobst | |
| 8,140,349 | B2 | | 3/2012 | Hanson et al. | |
| 8,231,585 | B2 | | 7/2012 | Heinz et al. | |
| 8,252,247 | B2 | | 8/2012 | Ferlic | |
| 8,257,286 | B2 | | 9/2012 | Meyer et al. | |
| 8,328,082 | B1 | | 12/2012 | Bochenko et al. | |
| 8,348,895 | B1 | | 1/2013 | Vitello | |
| 8,353,869 | B2 | | 1/2013 | Ranalletta et al. | |
| 8,413,410 | B2 | | 4/2013 | Ulm et al. | |
| 8,413,811 | B1 | * | 4/2013 | Arendt | A61C 8/0087 206/63.5 |
| 8,443,999 | B1 | | 5/2013 | Reinders | |
| D684,057 | S | | 6/2013 | Kwon | |
| 8,512,277 | B2 | | 8/2013 | Del Vecchio | |
| 8,528,757 | B2 | | 9/2013 | Bisio | |
| 8,556,074 | B2 | | 10/2013 | Turner et al. | |
| 8,579,116 | B2 | | 11/2013 | Pether et al. | |
| 8,591,462 | B1 | | 11/2013 | Vitello | |
| 8,597,255 | B2 | | 12/2013 | Emmott et al. | |
| 8,597,271 | B2 | | 12/2013 | Langan et al. | |
| 8,616,413 | B2 | | 12/2013 | Koyama | |
| D701,304 | S | | 3/2014 | Lair et al. | |

(56) References Cited

U.S. PATENT DOCUMENTS 8,672,902 B2 3/2014 Ruan et al.
8,702,674 B2 4/2014 Bochenko
8,777,910 B2 7/2014 Bauss et al.
8,777,930 B2 7/2014 Swisher et al.
8,852,561 B2 10/2014 Wagner et al.
8,864,021 B1 10/2014 Vitello
8,864,707 B1 10/2014 Vitello
8,864,708 B1 10/2014 Vitello
8,911,424 B2 12/2014 Weadock et al.
8,945,082 B2 2/2015 Geiger et al.
8,978,909 B2 3/2015 Kakutani et al.
9,016,473 B2 4/2015 Tamarindo
9,027,769 B2 5/2015 Willows et al.
9,082,157 B2 7/2015 Gibson
9,095,667 B2 8/2015 Von Schuckman
9,101,534 B2 8/2015 Bochenko
D738,495 S 9/2015 Strong et al.
9,125,976 B2 9/2015 Uber, III et al.
D743,019 S 11/2015 Schultz
9,192,443 B2 11/2015 Tennican
9,199,042 B2 12/2015 Farrar et al.
9,199,749 B1 12/2015 Vitello et al.
9,220,486 B2 12/2015 Schweiss et al.
9,220,577 B2 12/2015 Jessop et al.
9,227,019 B2 1/2016 Swift et al.
D750,228 S 2/2016 Strong et al.
9,272,099 B2 3/2016 Limaye et al.
9,311,592 B1 4/2016 Vitello et al.
D756,777 S 5/2016 Berge et al.
9,336,669 B2 5/2016 Bowden et al.
D759,486 S 6/2016 Ingram et al.
D760,384 S 6/2016 Niunoya et al.
D760,902 S 7/2016 Persson
9,402,967 B1 8/2016 Vitello
9,427,715 B2 8/2016 Palazzolo et al.
9,433,768 B2 9/2016 Tekeste et al.
9,463,310 B1 10/2016 Vitello
D773,043 S 11/2016 Ingram et al.
9,480,801 B2 11/2016 Schiller et al.
D777,903 S 1/2017 Schultz
9,662,456 B2 5/2017 Woehr
D789,529 S 6/2017 Davis et al.
9,687,249 B2 6/2017 Hanlon et al.
9,694,948 B1 7/2017 Pakhomov et al.
9,744,304 B2 8/2017 Swift et al.
D797,928 S 9/2017 Davis et al.
D797,929 S 9/2017 Davis et al.
9,764,098 B2 9/2017 Hund et al.
9,821,152 B1 11/2017 Vitello et al.
D806,241 S 12/2017 Swinney et al.
D807,503 S 1/2018 Davis et al.
9,855,191 B1 1/2018 Vitello et al.
D815,945 S 4/2018 Fischer
9,987,438 B2 6/2018 Stillson
D825,746 S 8/2018 Davis et al.
10,039,913 B2 8/2018 Yeh et al.
D831,201 S 10/2018 Holtz et al.
D834,187 S 11/2018 Ryan
10,124,122 B2 11/2018 Zenker
10,166,343 B1 1/2019 Hunt et al.
10,166,347 B1 1/2019 Vitello
10,183,129 B1 1/2019 Vitello
10,207,099 B1 2/2019 Vitello
D842,464 S 3/2019 Davis et al.
D847,373 S 4/2019 Hurwit et al.
10,293,987 B2 5/2019 Sattig et al.
10,300,263 B1 5/2019 Hunt
10,307,548 B1 6/2019 Hunt et al.
10,315,024 B1 6/2019 Vitello et al.
10,315,808 B2 6/2019 Taylor et al.
10,376,655 B2 8/2019 Pupke et al.
D859,125 S 9/2019 Weagle et al.
10,478,262 B2 11/2019 Niese et al.
10,555,872 B1 2/2020 Thorne
10,618,711 B2 4/2020 Weir
10,695,490 B2 6/2020 Perazzo et al.
10,758,684 B1 9/2020 Vitello et al.
10,773,067 B2 9/2020 Davis et al.
10,800,556 B2 10/2020 Thorne et al.
D903,865 S 12/2020 Banik et al.
10,888,672 B1 1/2021 Vitello
10,898,659 B1 1/2021 Vitello et al.
10,912,898 B1 2/2021 Vitello et al.
10,933,202 B1 3/2021 Banik
10,940,087 B2 3/2021 Thorne et al.
10,953,162 B1 3/2021 Hunt et al.
11,040,149 B1 6/2021 Banik
11,040,154 B1 6/2021 Vitello et al.
11,065,181 B2 7/2021 Davis et al.
11,097,071 B1 8/2021 Hunt et al.
11,168,818 B2 11/2021 Fangrow
11,278,681 B1 3/2022 Banik et al.
D948,713 S 4/2022 Banik
11,357,588 B1 * 6/2022 Vitello ................ A61M 5/3205
11,413,406 B1 8/2022 Vitello et al.
11,426,328 B1 8/2022 Ollmann et al.
11,471,610 B1 10/2022 Banik et al.
11,523,970 B1 12/2022 Vitello et al.
11,541,180 B1 1/2023 Vitello et al.
11,690,994 B1 7/2023 Banik et al.
11,697,527 B1 7/2023 Hendren et al.
11,779,520 B1 10/2023 Vitello
11,793,987 B1 10/2023 Vitello et al.
11,850,210 B2 12/2023 Dadachanji et al.
11,857,751 B1 1/2024 Vitello
11,872,187 B1 1/2024 Vitello et al.
11,904,149 B1 2/2024 Vitello et al.
11,911,339 B1 2/2024 Lehel et al.
12,070,591 B1 8/2024 Vitello
12,172,803 B1 12/2024 Vitello et al.
12,195,241 B1 1/2025 Vitello et al.
12,201,230 B2 1/2025 Bell
12,383,463 B1 8/2025 Vitello et al.
2001/0003150 A1 6/2001 Imbert
2001/0034506 A1 10/2001 Hirschman et al.
2001/0056258 A1 12/2001 Evans
2002/0007147 A1 1/2002 Capes et al.
2002/0023409 A1 2/2002 Py
2002/0046962 A1 * 4/2002 Vallans ................ A61B 50/362
206/370
2002/0079281 A1 6/2002 Hierzer et al.
2002/0097396 A1 7/2002 Schafer
2002/0099334 A1 7/2002 Hanson et al.
2002/0101656 A1 8/2002 Blumenthal et al.
2002/0104770 A1 8/2002 Shapeton et al.
2002/0133119 A1 9/2002 Eakins et al.
2003/0041560 A1 3/2003 Kemnitz
2003/0055685 A1 3/2003 Cobb et al.
2003/0146617 A1 8/2003 Franko, Sr.
2003/0183547 A1 10/2003 Heyman
2003/0187403 A1 10/2003 Balestracci
2004/0008123 A1 1/2004 Carrender et al.
2004/0064095 A1 4/2004 Vitello
2004/0116858 A1 6/2004 Heinz et al.
2004/0129738 A1 7/2004 Stukas
2004/0173563 A1 9/2004 Kim et al.
2004/0186437 A1 9/2004 Frenette et al.
2004/0225258 A1 11/2004 Balestracci
2005/0146081 A1 7/2005 MacLean et al.
2005/0148941 A1 7/2005 Farrar et al.
2005/0209555 A1 9/2005 Middleton et al.
2006/0049948 A1 3/2006 Chen et al.
2006/0084925 A1 4/2006 Ramsahoye
2006/0089601 A1 4/2006 Dionigi
2006/0169611 A1 * 8/2006 Prindle ................ A61M 5/002
206/364
2006/0173415 A1 8/2006 Cummins
2006/0189933 A1 8/2006 Alheidt et al.
2007/0060898 A1 3/2007 Shaughnessy et al.
2007/0106234 A1 5/2007 Klein
2007/0142786 A1 6/2007 Lampropoulos et al.
2007/0191690 A1 8/2007 Hasse et al.
2007/0219503 A1 9/2007 Loop et al.
2007/0257111 A1 11/2007 Ortenzi

(56) References Cited

U.S. PATENT DOCUMENTS

2008/0068178 A1 3/2008 Meyer
2008/0078146 A1 4/2008 Cirio
2008/0097310 A1 4/2008 Buehler et al.
2008/0106388 A1 5/2008 Knight
2008/0140020 A1 6/2008 Shirley
2008/0243088 A1 10/2008 Evans
2008/0302711 A1 12/2008 Windmiller
2008/0303267 A1 12/2008 Schnell et al.
2008/0306443 A1 12/2008 Neer
2009/0008356 A1 1/2009 Gadzic et al.
2009/0084804 A1 4/2009 Caspary et al.
2009/0099552 A1 4/2009 Levy et al.
2009/0149815 A1 6/2009 Kiel et al.
2009/0166311 A1 7/2009 Claessens
2009/0212954 A1 8/2009 Adstedt et al.
2009/0326481 A1 12/2009 Swisher et al.
2010/0050351 A1 3/2010 Colantonio et al.
2010/0051491 A1* 3/2010 Lampropoulos ...... A61M 5/008 206/366
2010/0084403 A1 4/2010 Popish et al.
2010/0089862 A1 4/2010 Schmitt
2010/0126894 A1 5/2010 Koukol et al.
2010/0179822 A1 7/2010 Reppas
2010/0211016 A1 8/2010 Palmer-Felgate
2010/0228226 A1 9/2010 Nielsen
2010/0252564 A1 10/2010 Martinez et al.
2010/0283238 A1 11/2010 Deighan et al.
2010/0307108 A1 12/2010 Sink et al.
2011/0009836 A1 1/2011 Chebli et al.
2011/0044850 A1 2/2011 Solomon et al.
2011/0046550 A1 2/2011 Schiller et al.
2011/0046603 A1 2/2011 Felsovalyi et al.
2012/0064515 A2 3/2012 Knapp et al.
2012/0096957 A1 4/2012 Ochman
2012/0110950 A1 5/2012 Schraudolph
2013/0018356 A1 1/2013 Prince et al.
2013/0018536 A1 1/2013 Prince et al.
2013/0056130 A1 3/2013 Alpert et al.
2013/0088354 A1 4/2013 Thomas
2013/0145725 A1 6/2013 Bianco et al.
2013/0237949 A1 9/2013 Miller
2013/0269592 A1 10/2013 Heacock et al.
2014/0000781 A1 1/2014 Franko, Jr.
2014/0034536 A1 2/2014 Reinhardt et al.
2014/0069202 A1 3/2014 Fisk
2014/0069829 A1 3/2014 Evans
2014/0076840 A1 3/2014 Graux et al.
2014/0135738 A1 5/2014 Panian
2014/0155868 A1 6/2014 Nelson et al.
2014/0163465 A1 6/2014 Bartlett, II et al.
2014/0257843 A1 9/2014 Adler et al.
2014/0319141 A1 10/2014 Stratis et al.
2014/0326727 A1 11/2014 Jouin et al.
2014/0353196 A1 12/2014 Key
2014/0358078 A1 12/2014 Fischer et al.
2015/0013811 A1 1/2015 Carrel et al.
2015/0048045 A1 2/2015 Miceli et al.
2015/0112296 A1 4/2015 Ishiwata et al.
2015/0136632 A1* 5/2015 Moir ...................... B65D 43/22 206/778
2015/0182686 A1 7/2015 Okihara
2015/0191633 A1 7/2015 De Boer et al.
2015/0246185 A1 9/2015 Heinz
2015/0251820 A1 9/2015 Glaser et al.
2015/0302232 A1 10/2015 Strassburger et al.
2015/0305982 A1 10/2015 Bochenko
2015/0310771 A1 10/2015 Atkinson et al.
2016/0067144 A1 3/2016 Chang
2016/0067422 A1 3/2016 Davis et al.
2016/0090456 A1 3/2016 Ishimaru et al.
2016/0136352 A1 5/2016 Smith et al.
2016/0144119 A1 5/2016 Limaye et al.
2016/0158110 A1 6/2016 Swisher et al.
2016/0158449 A1 6/2016 Limaye et al.
2016/0176550 A1 6/2016 Viitello et al.
2016/0194121 A1 7/2016 Ogawa et al.
2016/0250420 A1 9/2016 Maritan et al.
2016/0279032 A1 9/2016 Davis
2016/0328586 A1 11/2016 Bowden et al.
2016/0361235 A1 12/2016 Swisher
2016/0367439 A1 12/2016 Davis et al.
2017/0007771 A1 1/2017 Duinat et al.
2017/0014310 A1 1/2017 Hyun et al.
2017/0124289 A1 5/2017 Hasan et al.
2017/0173321 A1 6/2017 Davis et al.
2017/0203086 A1 7/2017 Davis
2017/0225843 A1 8/2017 Glaser et al.
2017/0239141 A1 8/2017 Davis et al.
2017/0297781 A1 10/2017 Kawamura
2017/0319438 A1 11/2017 Davis et al.
2017/0328758 A1 11/2017 Fuchs
2017/0349335 A1 12/2017 Sattig et al.
2017/0354792 A1 12/2017 Ward
2018/0001540 A1 1/2018 Byun
2018/0014998 A1 1/2018 Yuki et al.
2018/0064604 A1 3/2018 Drmanovic
2018/0078684 A1 3/2018 Peng et al.
2018/0089593 A1 3/2018 Patel et al.
2018/0098915 A1 4/2018 Rajagopal et al.
2018/0147115 A1 5/2018 Nishioka et al.
2018/0236177 A1 8/2018 Schraga
2018/0312305 A1 11/2018 Rognard
2019/0308006 A1 10/2019 Erekovcanski et al.
2019/0388626 A1 12/2019 Okihara
2021/0244892 A1 8/2021 Maritan et al.
2022/0008645 A1 1/2022 Ukai et al.
2022/0024630 A1 1/2022 Bohamed
2022/0339067 A1 10/2022 Christine et al.

FOREIGN PATENT DOCUMENTS

EP 269920 6/1988
EP 571980 12/1993
EP 2724977 4/2014
GB 486367 6/1938
JP 08002544 1/1996
KR 101159987 6/2012
WO WO1992003348 3/1992
WO WO2008000279 1/2008
WO WO2017086607 5/2015

* cited by examiner

NEEDLE PACKAGING AND DISPOSAL ASSEMBLY

BACKGROUND OF THE INVENTION

This patent application is a Continuation application of, and a claim of priority is made to an earlier filed application having a filing date of Jun. 14, 2022 and Ser. No. 17/840,442, as well as an earlier filed application having a filing date of Nov. 25, 2020 and Ser. No. 17/104,807, which matured into U.S. Pat. No. 11,357,588 on Jun. 14, 2022, which also claimed priority to an earlier filed Provisional patent application having Ser. No. 62/939,958 and a filing date of Nov. 25, 2019, with the contents of these prior applications being incorporated herein by reference in their entireties.

FIELD OF THE INVENTION

The present invention is directed to a package assembly for at least one needle structure, operative to provide access thereto when in an open orientation and structured to accomplish safe disposal of the needle, subsequent to use, when in a closed orientation.

DESCRIPTION OF THE RELATED ART

In numerous medical care facilities, it is common practice to administer various medications to a patient either orally or by injection. As a result, a number of syringes, IV bags, medication carrying containers, etc. may be pre-loaded within or supplied to a medical care facility, and subsequently stored at different locations and/or stations throughout the facility. For example, at some large medical facilities, preloaded syringes or other administering containers may be delivered to multiple nurses' stations. Because of the remote location of many nurse's stations, however, a pre-loaded syringe is often given to other personnel for delivery to a patient's room and/or for subsequent dosing of the patient by a duly qualified nurse or other medically trained person.

Also, in the case of a very expensive drug or an addictive type drug such as, but not limited to morphine, there is a danger that the pre-loaded container will be tampered with at some point, by a person seeking to improperly gain unauthorized access to the drug. This possibility can present real danger when unauthorized access to the contents of the preloaded syringe, IV bag or other container is accomplished. One possible outcome of such a situation includes the inappropriate substitution of some other, unauthorized material in the syringe or container. By way of an example only, if saline solution were substituted for a dose of morphine, this could have serious consequences. Thus, there is a problem of determining if a sealed, preloaded medication container has, or has not, been exposed to contamination or might otherwise have been compromised by it being tampered with.

However, certain problems remain in the relevant field of art. By way of example, during sterile compounding, hospital pharmacists and other compounding operators need to use various needles to fill, extract from or filter in containers while maintaining an aseptic technique. Since needles of the type referred to come in sterile packaging, usually in blister packaging with a guard or sleeve to prevent users from potential puncture hazards, such packaging frequently requires the packaging to be opened and removed from the needle, in order to make the needle readily available for sterile preparation and/or use. Once the filling or other procedure involving the needle is complete, a user must maintain the aseptic technique while trying to replace the needle guard, frequently having to use only one hand. This creates a challenge and potentially dangerous situation, while at the same time adding time delay to the overall process.

Therefore, there is a need in this area for an improved assembly or structure preferably in the form of a packaging and disposal assembly or structure, which is capable of maintaining safe, sterile conditions of various types of needles, such as those used in medical procedures of the type set forth herein. Moreover, the structural and operative features of any such improved and proposed assembly for overcoming the disadvantages set forth herein, should allow for a preferred positioning of the needle, once the packaging and disposing assembly has been opened. If any such assembly were developed, it would preferably allow for positioning of the needle to facilitate its access, whether on a single use or a repetitive use basis. Further, it would be preferable if subsequent to use, the needle could be reinserted within interior portions of the packaging and disposing assembly, and thereafter disposed and maintained in a closed orientation. The goal of any such assembly would be for the needle and the packaging and disposal assembly, once in the aforementioned closed orientation, to all be discarded without fear of puncture, contamination, etc.

Further, if any such proposed and improved packaging and disposing assembly were developed, it would also be ideal if it could be formed of an appropriate plastic material which is low in cost, relatively easy to utilize during a manufacturing process and yet sufficiently durable to facilitate reliable and efficient storage and disposal of a needle structure respectively, before and after use.

SUMMARY OF THE INVENTION

The present invention is directed to a package assembly for a needle structure such as, but not limited to, a medical needle of the type which may be associated with a syringe or other type of medical container, instrument or device. In addition, the operative structuring of the package assembly facilitates the safe disposal of the needle, subsequent to its use. As set forth in greater detail hereinafter, other advantageous features of the present invention include the disposition of the contained needle in a position which facilitates repeated or singular access thereto, when the needle is being utilized.

In more specific terms, the package assembly of the present invention comprises a housing including at least one, but possibly a plurality of containment structures. Each of the containment structures is dimensioned and configured to removably contain a needle, of the type described herein. Further, each of the one or more containment structures comprises a base and a needle retaining segment movably interconnected to one another by a hinge. The hinge is integrally or fixedly attached to a correspondingly positioned longitudinal end of each of the base and retaining segment, thereby at least partially defining a substantially clamshell configuration of the housing. As such, the hinge is oriented in transverse relation and/or substantially perpendicular to the length of the containment structure, specifically including cooperatively positioned ones of the base and retaining segment. The hinge is disposed and structured to facilitate selective positioning of corresponding ones of the base and retaining segment into and between a closed orientation and an open orientation.

In at least one additional embodiment, wherein the housing includes a plurality of containment structures, the aforementioned hinge may be common to each of the containment structures. In the alternative, each of a plurality of operatively independent hinges or hinge segments may be associated with different ones of each of the plurality of containment structures. Moreover, in each of the structurally modified embodiments of the hinge and/or hinge segments, the base and the retaining segment of each containment structure may be independently or concurrently disposed in and between the closed orientation and the open orientation.

As indicated, the hinge may be integrally or otherwise fixedly secured to corresponding longitudinal ends of each of the base and retaining segment. Accordingly, the hinge may be more specifically defined as a "living hinge" formed of the same or other appropriate material from which the housing and one or more containment structures are formed. For purposes of clarification, a living hinge is a type of hinge made of a thin flexible material, typically plastic, wherein the plastic material may vary dependent, at least in part, on the intended use of the hinged components. Advantages of using a living hinge is the ability to be continuously and repeatedly bent and/or flexed without breaking or damage. This is due, at least in part, to the creation of at least minimal friction during the operative flexing of a living hinge. Further, recognized advantages of the living hinge include a thin design requiring minimal space for the intended use, as well as the ability to be effectively used in moist or other environments where other type hinges may demonstrate wear, damage, corrosion, etc. Also, the living hinge is quiet and inexpensive, thereby facilitating its reliable use in a variety of different practical applications. However, it should be noted that hinge structures and designs, other than a living hinge may be utilized in the movable interconnection of the base and retaining segment of each of the one or more containment structures of the packaging and disposing assembly or structure of the present invention.

Yet additional structural details of the present invention include the needle retaining segment of each of the one or more containment structures comprising a compartment dimensioned and structured to retain at least one needle therein. The compartment includes an elongated configuration having a hollow interior extending along at least a majority of the length thereof and an access opening disposed in direct communication with the hollow interior. Further, the access opening is formed on and at least partially defines a one longitudinal end of the compartment disposed in substantially opposing relation to the location of the aforementioned hinge. When the base and retaining segment of the one or more containment structures are disposed in the aforementioned open orientation, the access opening, as well as the needle contained within the corresponding compartment, is readily accessible.

Accordingly, accessibility to the contained needle within the compartment via the access opening is yet another feature of the packaging and disposing assembly of the present invention. Such accessibility is further enhanced by the structuring of the corresponding hinge to maintain a predetermined angular orientation of the retaining segment and integrated compartment, upwardly and outwardly from the base of the same containment structure. Moreover, a preferred predetermined angular orientation of the retaining segment, compartment and contained needle may be defined as an acute angle. As practically utilized, the base of a given containment structure, when in an open orientation, may be disposed on a substantially horizontal supporting surface. In cooperation therewith, the retaining segment, compartment and contained needle will be disposed outwardly and/or upwardly therefrom into the aforementioned predetermined angle, such as but not limited to, an acute angle.

Therefore, the structuring of the hinge associated with a given containment structure is intended to normally bias the retaining segment into the predetermined angular relation to the base, to at least partially define the open orientation. It is also to be noted that such a predetermined angular orientation of the retaining segment, outwardly from the corresponding base will be substantially maintained, whether the needle remains in the compartment or is removed therefrom through the access opening. As will be explained in greater detail hereinafter, such a preferred, predetermined angular disposition of the retaining segment and the needle retained within the compartment, serves to position the needle for easy and possibly repetitious removal from and reinsertion within the compartment, during the utilization of the needle in the intended manner.

Yet additional features of the needle packaging and disposing assembly of the present invention includes the base comprising a chamber having a hollow interior extending along at least a majority of the length of the base. The chamber includes an open, inner longitudinal side extending along at least a majority of the length of the base. The open, inner longitudinal side is disposed, dimensioned and configured to receive the compartment of the needle retaining segment therein concurrent to a closed orientation. As such, the length as well as the interior dimension of the chamber is sufficient to enclose the compartment of the corresponding retaining segment, concurrent to the compartment passing through the open longitudinal side of the chamber as the containment structure moves into the closed orientation. Moreover, when in the closed orientation the access opening of the compartment will be at least partially closed or at least obstructed by interior surface portions of the chamber, thereby preventing inadvertent removal of a needle from the interior of the compartment, through the access opening. Also, the cooperative structuring between the compartment and the interior of the chamber is such as to effectively segregate and/or isolate a needle disposed within the compartment from the interior surfaces of the chamber.

Therefore, the structural and operative features of the packaging and dispensing assembly as noted herein facilitate the initial storage, transportation, and handling of the contained needle in a sterile environment, while the housing and one or more containment structures are in the closed orientation. However, upon reaching its intended destination of use, the one or more containment structures may be selectively disposed into the open orientation, thereby providing convenient access to the needle contained within the compartment of the corresponding retaining segment.

The housing of the present invention further includes a closure structured to removably secure the base and the needle retaining segment of the one or more containment structures in the closed orientation. In at least one embodiment, the closure includes a first closure segment and a second closure segment, each considered a part of the housing, and each connected to and movable with a different one of the base and the needle retaining segment. One or more embodiments of the present invention may further define the closure, and more specifically, each of the first and second closure segments as a flange extending outwardly from a corresponding one of the base and needle retaining segment. The flanges are removably secured in confronting relation to one another concurrent to the one or more containment structures being in the closed orientation. Additional structural features of the closure include the ability to repeatedly position the base and retaining segment of each of the one or more containment structures into and out of both the closed orientation and the open orientation.

Therefore, the assembly or structure of the present invention is also capable of facilitating safe disposal of the needle subsequent to its use. In more specific terms, after use the needle is reinserted within the interior of the compartment, through the access opening. The retaining segment and compartment with the needle contained therein, is then selectively positioned from the open orientation into the closed orientation. In order to assure safe and reliable disposal of the needle, the intended design and structuring of the closure will maintain the base and retaining segment, of each of the one or more containment structures, in the closed orientation, absent an appropriately sufficient force to separate the base and the needle retaining segment. Once in the closed orientation, the entire housing and the one or more containment structures, as well as the used needles, may be appropriately discarded.

These and other objects, features and advantages of the present invention will become clearer when the drawings as well as the detailed description are taken into consideration.

BRIEF DESCRIPTION OF THE DRAWINGS

For a fuller understanding of the nature of the present invention, reference should be had to the following detailed description taken in connection with the accompanying drawings in which.

Like reference numerals refer to like parts throughout the several views of the drawings.

DETAILED DESCRIPTION OF THE PREFERRED EMBODIMENT

Figure 1:
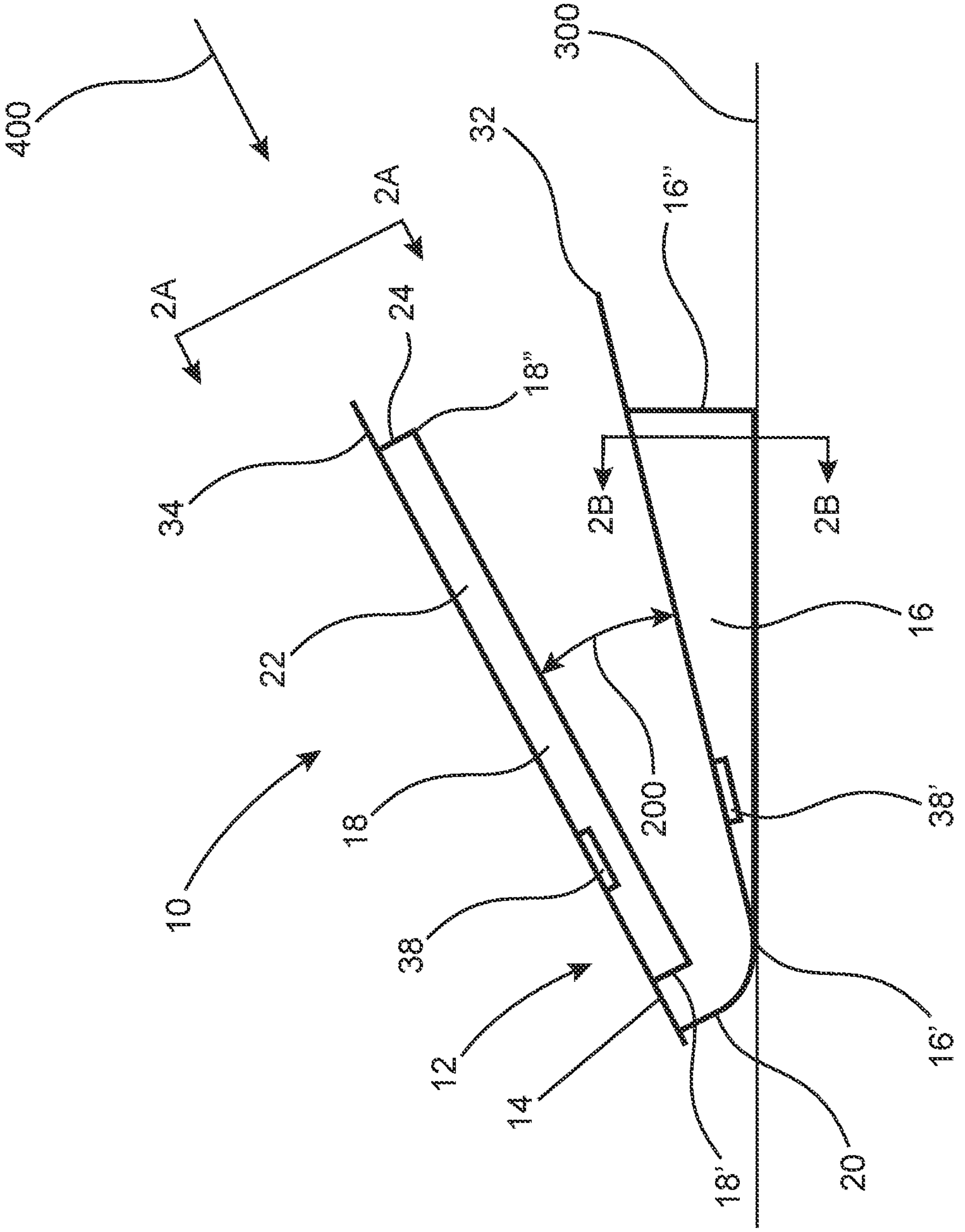
FIG. 1 is a side view of the packaging and disposal assembly of the present invention in an open orientation.
Figure 4:
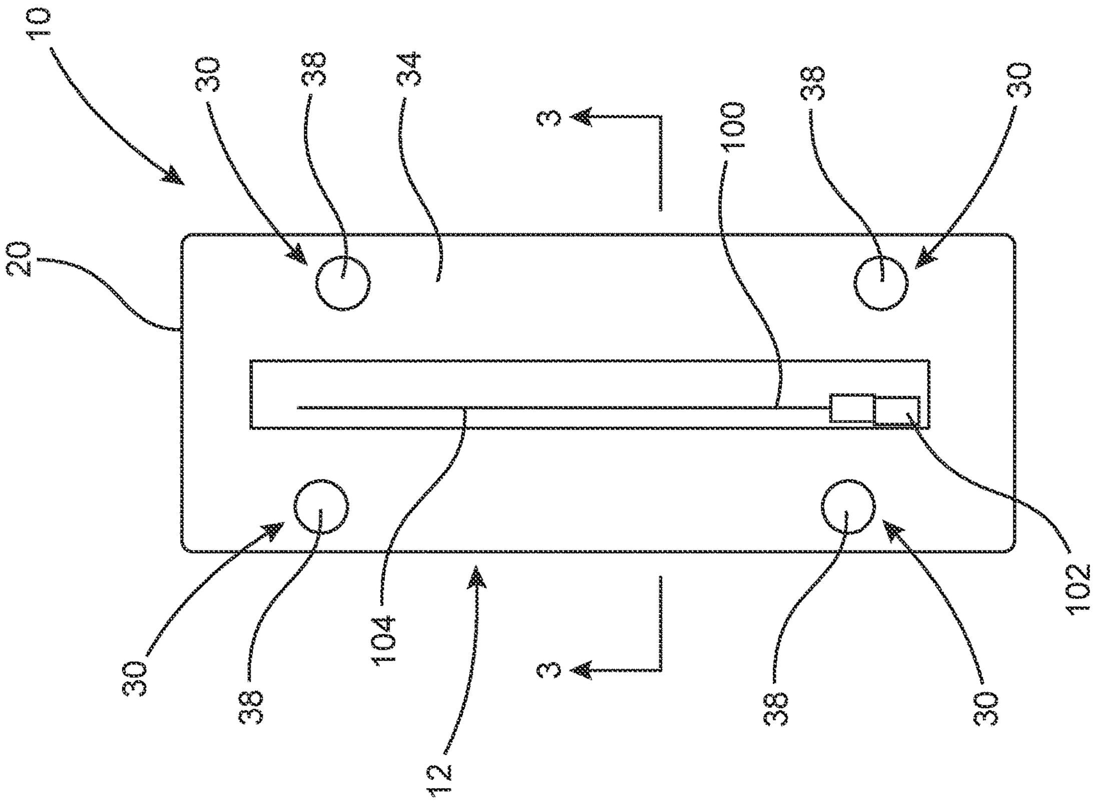
FIG. 4 is a top plan view of the embodiment of FIG. 1 in a closed orientation including a needle contained therein.

As shown in FIG. 1, the present invention is directed to a package and disposal assembly or structure generally indicated as 10 for a needle structure 100 (see also FIG. 4). The needle structure 100 can be, but is not limited to, a medical needle of the type which may be associated with a syringe or other type of medical instrument, container or device. Also, minor structural modifications of the assembly 10 may be made and still fall within the intended scope of the present invention to accommodate needle structures 100, which may vary in type and dimensions. In addition, the operative structuring of the package and disposal assembly 10 facilitates the safe discarding of the needle 100, subsequent to its use. As set forth in greater detail hereinafter, other advantageous features of the present invention include the disposition of the contained needle in a position which facilitates repeated or singular access thereto, when the needle 100 is being utilized.

In more specific terms, the assembly or structure 10 of the present invention comprises a housing generally indicated as 12 including at least one containment structure 14, as represented in FIGS. 1-4. However, and as explained in greater detail herein, the housing 12 may comprise a plurality of such containment structures 14, which would be generally attached to one another in laterally adjacent or contiguous, side-by-side relation. Each of the one or more containment structures 14 is dimensioned and configured to removably contain a needle 100, as explained in greater detail with reference to FIG. 4. Further, each of the one or more containment structures 14 comprises a base 16 and a needle retaining segment 18 movably connected to one another by a hinge 20. The hinge 20 is integrally or fixedly attached to a correspondingly positioned longitudinal ends 16' and 18' of the base 16 and retaining segment 18, thereby at least partially defining a substantially clamshell configuration of the housing 12. As such, the hinge 20 is oriented in substantially perpendicular or at least transverse relation to the length or longitudinal axis of the containment structure 14, specifically including cooperatively positioned ones of the base 16 and retaining segment 18. The hinge 20 is disposed and structured to facilitate selective positioning of the base 16 and retaining segment 18 into and between a closed orientation and an open orientation, respectively represented in FIGS. 3 and 1.

In at least one additional embodiment, wherein the housing 12 includes a plurality of containment structures 14 (not shown), the aforementioned hinge 20 may be common to each of the containment structures 14. In the alternative, a plurality of operatively independent hinges or hinge segments (not shown for purposes of clarity) may be structured and associated with different ones of each of the plurality of containment structures 14. Moreover, in each of the structurally modified embodiments of the hinge and/or hinge segments, the base 16 and the retaining segment 18 of each containment structure 14 may be independently or concurrently disposed in and between the closed orientation and the open orientation.

As indicated, the hinge 20 may be integrally or otherwise fixedly secured to corresponding longitudinal ends 16' and 18' of the base 16 and retaining segment 18. Accordingly, the hinge 20 may be more specifically defined as, but not limited to, a "living hinge" formed of the same or other appropriate material from which the housing 12 and one or more containment structures 14 are formed. This may be a plastic material although in one embodiment of the packaging and disposing assembly 10, the invention may be formed from a polyethylene terephthalate glycol-modified plastic (PETG) material which is produced by the copolymerization of polyethylene terephthalate (PET).

Advantages of using a living hinge include its ability to be continuously and repeatedly bent and/or flexed without breaking, deterioration or damage, due at least in part the existence of minimal friction, within the living hinge, during the operative flexing thereof. Therefore, recognized advantages of the living hinge include quiet operation, low cost and a relative thin and/or flat design requiring minimal space for its intended use and operation. Also, a living hinge may be effectively used in environments where other type hinges may demonstrate wear, corrosion, etc. However, it should be noted that hinge structures and designs, other than a living hinge may be utilized in the movable interconnection of the base 16 and retaining segment 18 of each of the one or more containment structures 14 of the packaging and disposal in assembly 10 of the present invention.

Figure 2A:
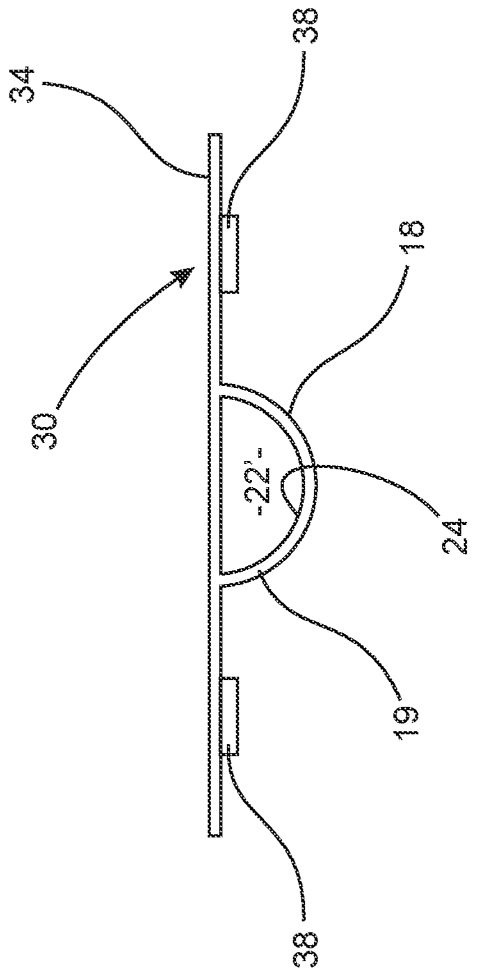
FIG. 2A is an end view along line 2A-2A of the embodiment of FIG. 1.
Figure 2B:
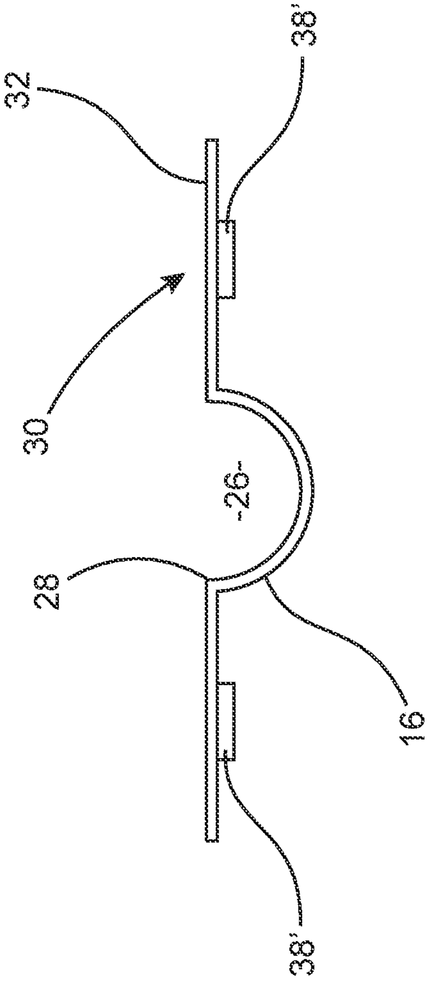
FIG. 2B is a sectional view along line 2B-2B of the embodiment of FIG. 1.

Yet additional structural details of the present invention include the needle retaining segment 18 of each of the one or more containment structures 14 comprising an interior compartment 22 dimensioned and configured to retain at least one needle 100 therein. The compartment 22 includes an elongated configuration having a hollow interior 22' extending along at least a majority of the length thereof and an access opening 24. The access opening 24 is disposed in direct communication with the hollow interior 22'. Further, the access opening 24 is formed on and at least partially defines a distal longitudinal end 18" of the compartment 22 and is further disposed in substantially opposing relation to the aforementioned hinge 20. As represented in FIG. 2A, the retaining segment 18 includes a substantially closed configuration extending along its length from the access opening 24 to the end 18'. Such a closed configuration is at least partially defined by the side wall 19 of the retaining segment 18 disposed in surrounding relation to and defining the borders of the interior compartment 22.

When the base 16 and retaining segment 18 of the one or more containment structures 14 are disposed in the aforementioned open orientation of FIG. 1, the access opening 24, as well as the needle 100 contained within the corresponding compartment 22, is readily accessible and removable from the compartment 22 via the access opening 24. Accordingly, accessibility to the contained needle 100 within the compartment 22 is yet another feature of the packaging and dispensing assembly 10 of the present invention. Such accessibility is further enhanced by the structuring of the corresponding hinge 20 to maintain a predetermined angular orientation, schematically represented as 200 in at least FIG. 1, of the retaining segment 18 disposed, upwardly and outwardly from the base 16 of the same containment structure 14. Moreover, a preferred predetermined angular orientation 200 of the retaining segment 18, compartment 20 and contained needle 100, relative to the base 16, may be defined as an acute angle. As practically utilized, the base 16 of a given containment structure 14, when in the open orientation of FIG. 1, may be disposed on a substantially horizontal supporting surface 300. In cooperation therewith, the retaining segment 18, compartment 22 and contained needle 100 will be disposed outwardly and/or upwardly from the base 16 into the aforementioned predetermined angle 200 such as, but not limited to an acute angle.

As used herein, the needle or needle structure 100 may be in the form of a medical needle of the type connected to a syringe or other medical instrument, container, etc. As such the needle 100 may include an attachment structure or "hub" 102 secured to one end thereof as represented in FIG. 4. Therefore, when utilized the hub 102, will commonly have a larger or bulkier dimension and configuration than that of the elongated potentially penetrating portion 104 of the needle 100. As a result of such a larger configuration and/or dimension, when the needle 100 is in use, the hub 102 may be positioned to extend at least partially outward from the access opening 24 and thereby be removably retained in such an exposed position, exteriorly of the access opening 24 and compartment 22. As a result, the exposed positioning of the hub 102 facilitates access to and removal of the needle 100 from the interior of the compartment 22, when the containment structure 14 is in the open orientation of FIG. 1, Therefore, the structuring of the hinge 20 associated with a given containment structure 14 is intended to normally bias the retaining segment 18 into the predetermined angular relation 200 relative to the base 16, to at least partially define the open orientation of FIG. 1. It is also to be noted that such a predetermined angular orientation 200 of the retaining segment 18, outwardly from the corresponding base 16, will be substantially maintained, whether the needle 100 remains in the compartment 22 or is removed therefrom through the corresponding access opening 24. As will be explained in greater detail hereinafter, such a preferred, predetermined angular disposition 200 of the retaining segment 18 and the needle 100 removably retained within the compartment 22 serves to position the needle 100 for easy individual and/or repeated access during the utilization of the needle 100 in the intended manner.

Yet additional features of the packaging and disposal assembly of the present invention includes the base 16 comprising a chamber 26 having a hollow interior extending along at least a majority of the length of the base 16 from a closed front end 16" to the opposite end 16', adjacent the hinge 20. The chamber 26 includes an open, inner longitudinal side 28 extending along at least a majority of the length of the base 16. The open inner, longitudinal side 28 is disposed, dimensioned and configured to receive the compartment 22 of the needle retaining segment 18 therein concurrent to a closed orientation. As such, the length as well as the interior dimension of the chamber 26 is sufficient to enclose the compartment 22 of the corresponding retaining segment 18, concurrent to the compartment 22 passing through the open longitudinal side 28 of the chamber 26 as the containment structure 14 moves into the closed orientation.

Further, the length as well as the interior dimension of the chamber 26 is sufficient to enclose the compartment 22 of the corresponding retaining segment 18, concurrent to the containment structure 14 being in the aforementioned closed orientation, as represented in FIGS. and 4. Moreover, when in the closed orientation, the access opening 24 will be at least partially closed or at least obstructed by interior surface of the closed end 16" of the base 16. The closing or blocking of the access opening 24 by the closed end 16" will prevent inadvertent removal of a contained needle 100 from the interior of the compartment 22, through the access opening 24, when the containment structure 14 is in the closed orientation. Also, the cooperative structuring between the compartment 22 and the interior of the chamber 26 is such as to effectively enclose at least a majority and in some embodiments an entirety of the compartment 22, as also represented in FIG. 4. Further, the enclosed disposition of the compartment 22 within the interior of the chamber 26 will result in a segregated positioning of the needle 100 from interior surface portions of the chamber 26, due at least in part to the closed configuration of the chamber 22 by the surrounding, enclosing side wall 19, as set forth herein.

Therefore, the structural and operative features of the packaging and dispensing assembly 10, as noted herein, facilitate the initial storage, transportation, and handling of the contained needle 100 in a sterile environment, while the housing 12 and the one or more containment structures 14 associated therewith are in the closed orientation. However, upon reaching its intended destination of use, the one or more containment structures 14 may be selectively disposed into the open orientation of FIG. 1, thereby providing convenient and facilitated access to the needle 100 within the compartment 22 of the corresponding retaining segment 18.

The housing 12 of the present invention further includes a closure, generally indicated as 30, structured to removably but securely maintain the base 16 and the needle retaining segment 18 of the one or more containment structures 14 in the closed orientation. In at least one embodiment, the closure 30 includes a first closure segment 32 and a second closure segment 34 each connected to and movable with a different portion of the housing 12, respectively connected to the base 16 and the needle retaining segment 18. Therefore, one or more embodiments of the present invention May further define the closure 30 and more specifically, the first and second closure segments 32 and 34 as a flange respectively extending outwardly from a corresponding one of the base 16 and needle retaining segment 18. In addition, the closure 30 includes at least one, but more practically, a plurality of pairs of cooperatively structured closure members 38 and 38', which are respectively formed in the closure segment flanges 32 and 34.

More specifically, one embodiment of the present invention includes the closure 30 comprising each of the one or more pairs of closure members 38, 38' comprising a protruding member 38 integrally formed in one of the flanges, such as at 34. In turn, closure member 38' may be a recess structure integrally formed in closure segment flange 32 and disposed and configured to removably receive the protruding member 38 therein. The at least minimal flexibility of the plastic material from which the closure members 38, 38' are formed facilitate a removable, snap-type connection therebetween. Further, the cooperative dimensioning between the closure members 38, 38' serve to maintain their attachment and in turn maintain the closed orientation of the containment structure 14, until a sufficient force is exerted on the base 16 and/or needle retaining segment 18 sufficient to cause a separation thereof into the open orientation. As also indicated herein, such a "sufficient force" should be such as to prevent or restrict the possibility of inadvertent separation of the base 16 and retaining segment 18 when in the closed orientation, in order to assure safe disposal of the needle 100 subsequent to use.

Figure 3:
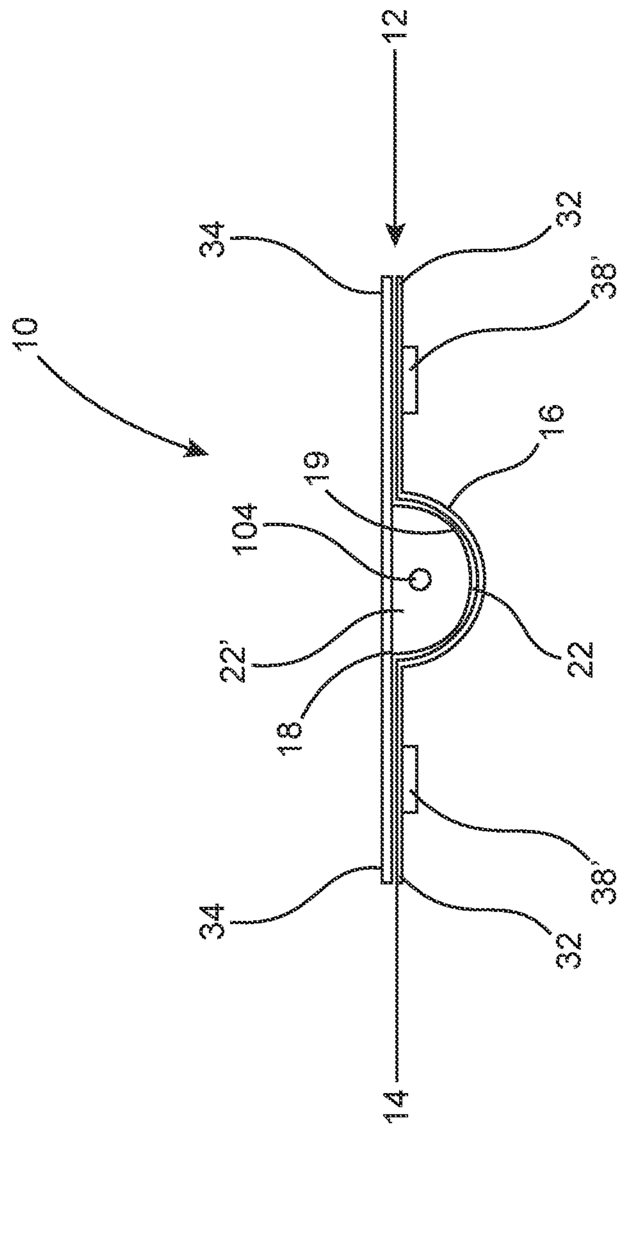
FIG. 3 is a sectional view along line 3-3 of the embodiment of FIG. 4.

Accordingly, as represented in FIG. 3, the closure segment flanges 32 and 34 are removably secured in confronting relation to one another concurrent to the one or more containment structures 14 being in the closed orientation. Additional structural features of the closure 30, including the at least one pair of closure members 38 and 38', include its ability to repeatedly position corresponding ones of the base 16 and retaining segment 18 of each of the one or more containment structures 14 into and out of both the closed orientation of FIG. 3 and the open orientation of FIG. 1.

Therefore, the packaging and disposal assembly or structure 10 of the present invention is capable of facilitating safe disposal of the needle 100 subsequent to its use. More specifically, after use, the needle 100 is disposed within the interior of the compartment 22, through the access opening as represented by directional arrow 400. The retaining segment 18 and compartment 22, with the needle 100 contained therein, is then selectively positioned from the open orientation into the closed orientation. The structuring of the of the closure assembly 30 including the one or more pair of closure members 38, 38', will maintain the base 16 and retaining segment 18 of each of the one or more containment structures 14 in the closed orientation of FIG. 3. Once in the closed orientation, the entire housing 12, the one or more containment structures 14 as well as subsequently used one or more needles 100 may be appropriately discarded. In order to assure safe and reliable disposal, the aforementioned closure 30 is specifically structured to maintain the housing and containment structure in the closed orientation until a "sufficient force" is applied to the housing 12, in the manner at least generally set forth above.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. An assembly for packaging and disposing of a needle, said assembly comprising:

a housing including at least one containment structure, said containment structure comprising a base and a needle retaining segment, a hinge attached to and movably interconnecting said base and said needle retaining segment between a closed orientation and an open orientation, said needle retaining segment comprising a compartment including a closed hollow interior, said closed hollow interior dimensioned and structured to removably retain the needle therein, concurrent to said open orientation and said closed orientation, said hinge including a biased construction structured to normally bias said housing in said open orientation, said open orientation comprising said needle retaining segment and said compartment separated from said base and extending outwardly therefrom in a predetermined angular relation thereto, and said closed orientation at least partially defined by said compartment disposed within said base, and said closed hollow interior disposed in segregated relation to an interior of said base.

2. The assembly as recited in claim 1 wherein said predetermined angular relation comprises said needle retaining segment and said closed hollow interior disposed outwardly from and connected to said base at an acute angle.

3. The assembly as recited in claim 1 wherein said hinge comprises a living hinge, said living hinge disposed at one end of said housing, and extending in transverse relation to a length of said base and said needle retaining segment.

4. The assembly as recited in claim 1 wherein said base comprises a chamber formed therein; said closed orientation at least partially defined by said compartment disposed within said chamber and said closed hollow interior disposed in segregated relation to an interior of said chamber.

5. The assembly as recited in claim 1 wherein said housing comprises, a closure structured to removably secure said base and said needle retaining segment in said closed orientation; said closure comprising a first closure segment and a second closure segment respectively connected to and movable with said base and said needle retaining segment.

6. The assembly as recited in claim 5 wherein each of said first and second closure segments comprises a flange extending outwardly from a corresponding one of said base and said needle retaining segment; said flanges removably secured in confronting relation to one another, concurrent to said closed orientation.

7. The assembly as recited in claim 1 wherein said predetermined angular relation comprises said needle retaining segment and said compartment disposed outwardly from said base at an acute angle.

8. The assembly as recited in claim 1 wherein said compartment further includes a needle access opening disposed in direct communication with said closed hollow interior.

9. The assembly as recited in claim 8 wherein said compartment and said closed hollow interior each include an elongated configuration, said hinge and said needle access opening disposed at opposite ends of said compartment.

10. The assembly as recited in claim 8 wherein said base comprises a chamber formed therein, said closed orientation at least partially defined by said compartment enclosed within said chamber.

11. The assembly as recited in claim 10 wherein said closed orientation further comprises an interior of said chamber being disposed in at least partially closing, obstructing relation to said needle access opening.

12. The assembly as recited in claim 11 wherein said open orientation comprises disposition of said closed hollow interior in an accessible position via said needle access opening.

13. The assembly as recited in claim 12 wherein said predetermined angular relation comprises said compartment and said closed hollow interior disposed outwardly from said base at an acute angle.

14. The assembly as recited in claim 8 wherein said closed hollow interior is disposed in an accessible orientation, via said needle access opening, concurrent to said compartment disposed in said predetermined angular orientation.

15. The assembly as recited in claim 8 wherein said compartment further comprises a side wall disposed in at least partially surrounding relation to and defining boundaries of said closed hollow interior.

16. The assembly as recited in claim 15 wherein said needle access opening is disposed at one end of said side wall substantially opposite to a location of said hinge.

17. The assembly as recited in claim 1 wherein said compartment further comprises a side wall disposed at least partially surrounding relation to and defining boundaries of said closed hollow interior.

18. The assembly as recited in claim 8 where in each of said closure segments include a closure member, said closure members cooperatively disposed for a mating with one another, concurrent to said closed orientation.

19. The assembly as recited in claim 18 wherein each of said closure members are cooperatively structured to define a removable, snap-type connection therebetween.

* * * * *